United States Patent [19]
Ogilvie et al.

[11] Patent Number: 6,015,798
[45] Date of Patent: Jan. 18, 2000

[54] METHOD FOR REDUCING THE DAMAGING EFFECTS OF RADIATION THERAPY ON ANIMAL SKIN AND MUCOSA

[75] Inventors: Gregory K. Ogilvie, Ft. Collins, Colo.; Deborah J. Davenport, Lecompton, Kans.; Kathy L. Gross, Topeka, Kans.; Michael S. Hand, Maple Hill, Kans.

[73] Assignees: Colgate Palmolive Company, New York, N.Y.; Colorado State University Research Foundation, Ft. Collins, Colo.

[21] Appl. No.: 09/106,295

[22] Filed: Jun. 29, 1998

Related U.S. Application Data

[63] Continuation-in-part of application No. 08/544,421, Oct. 10, 1995, Pat. No. 5,776,913.

[51] Int. Cl.[7] ...................... A61K 31/715; A61K 31/685; A61K 31/20; A61K 31/195

[52] U.S. Cl. .................. 514/57; 514/60; 514/77; 514/78; 514/558; 514/560; 514/564

[58] Field of Search ................. 514/57, 77, 78, 514/60, 558, 560, 564

[56] References Cited

U.S. PATENT DOCUMENTS 5,776,913  7/1998  Ogilvie et al. ............................ 514/57

*Primary Examiner*—Alan L. Rotman
*Attorney, Agent, or Firm*—Paul Shapiro

[57] ABSTRACT

The severity of damage caused to the skin and mucosa of animals with cancer undergoing radiation therapy is mitigated by feeding the animal a nutritionally balanced food composition containing omega-6 polyunsaturated fatty acids which are supplemented with a mixture of a omega-3 polyunsaturated fatty acids and arginine.

5 Claims, No Drawings

METHOD FOR REDUCING THE DAMAGING EFFECTS OF RADIATION THERAPY ON ANIMAL SKIN AND MUCOSA

RELATED APPLICATION

This application is a continuation-in-part of U.S. Ser. No. 08/544,421 filed Oct. 10, 1995, now U.S. Pat. No. 5,776,913.

BACKGROUND OF THE INVENTION

1. Field of the Invention

The present invention relates to a method of reducing damage to skin and mucosa in pet animals such as dogs and cats wherein the pet is afflicted with cancer and is subjected to radiation therapy, the method including a food composition to be used for this purpose.

2. The Prior Art

Clinical radiation therapy in animals with cancer is known to induce biochemical changes in normal animal tissues and cells resulting in damage thereto. A need clearly exists for means to ameliorate the damage to a patient's normal tissues during radiation therapy. Previous methods of affording such amelioration include the administration to the patient of chemical agents which often have undesirable side effects on the patient.

SUMMARY OF THE INVENTION

The present invention is premised on the discovery that radiation damage to normal cells of animals with cancer undergoing radiation therapy can be reduced by fortifying the animal with a diet supplemented with a mixture of polyunsaturated omega-3 fatty acids and arginine.

DETAILED DESCRIPTION OF THE PREFERRED EMBODIMENTS

The method of reducing the damaging effects of radiation therapy in animals with cancer, and particularly pet animals, pursuant to the present invention, is provided by feeding the animal undergoing such therapy with a food composition which contains omega-6 fatty acids as a nutrient and in which the nutrient content of the food is supplemented to contain on a dry matter basis about 2.5 to about 7.5% omega-3 fatty acids, and about 2.0 to about 3.5% arginine, the weight ratio of omega-3 to omega-6 fatty acid in the food being in the range of about 0.3:1 to 3.5:1.

It is particularly advantageous in the practice of the present invention that the nutrient content of the food composition used in the method contain about 27 to about 35% on a dry matter basis of fat and about 15 to about 27% on a dry matter of carbohydrate, the term "dry matter basis" when used herein meaning the nutrient content of the food product after moisture is removed. A food composition of this type is disclosed in co-pending patent application U.S. Ser. No. 08/544,421, which composition is effective in mitigating the severity of metabolic disturbances in animals with cancer. The art however has provided no link between feeding this food composition to animals with cancer to reduce metabolic disturbance and the reduction in damage to normal skin and mucosa cells when such animals, having been fed such food, are exposed to radiation therapy.

The present invention is generally intended to apply to all forms of pet food including dry, canned or intermediate moisture pet food products, as these terms are recognized by those skilled in the art of pet food formulation and manufacturing, which foods conventionally contain omega-6 fatty acids as essential nutritional ingredients.

The pet food composition of the present invention is not intended to be restricted by any specific listing of proteinaceous, fat or carbohydrate ingredients or product form, since these will be entirely dependent upon the nutritional balance of the ration desired as well as their availability to the pet food manufacturer. Generally, aside from nutritionally balancing ingredients such as vitamins, minerals and the like, the food compositions of the present invention have a moisture content of about 10 to about 90% by weight and preferably about 65 to about 75% by weight and are formulated having a nutrient content listed in Table I below.

TABLE I

| Nutrient | Nutrient Content % (Dry Matter Basis) |
|---|---|
| Carbohydrate | about 15 to about 27 |
| Protein | about 35 to about 48 |
| Fat | about 27 to about 35 |
| Omega-6 Fatty Acids | about 2.0 to about 6.0 |
| Omega-3 Fatty Acids | about 2.5 to about 7.5 |
| Arginine | about 2.0 to about 3.5 |
| Nutritional balancing agents such as vitamins (A, B1, B2, B6, E) and minerals (Ca, P, Na, K, Mg, Fe, Cl) | about 0.4 to about 1.0 |

The critical factor insofar as the present invention is applicable to the amelioration of radiation therapy cell damage is the presence of a mixture of omega-3 polyunsaturated fatty acids and arginine in the proportions specified in Table I above, in a nutritionally balanced pet food composition which includes omega-6 polyunsaturated fatty acids as nutrients.

The fat and carbohydrate nutrients used to prepare the pet food compositions of the present invention may be supplied by ingredients such as meat, meat by-products, other animal protein sources and grains as the food source. By meat is meant the flesh of cattle, swine, sheep, goat, horses, and other mammals as well as poultry and fish. Meat by-products include, but are not limited to lungs, kidneys, brain, livers, and stomachs and intestines freed of their contents. Additionally, meat, meat by-products, and other animal protein source mixtures are suitable for use in the pet food of this invention. The nutrient ingredients may also include amounts of cereal grains such as wheat, corn, barley and rice and fibrous bulking materials such as cellulose, beet pulp, peanut hulls or soy fiber.

A typical canned dog food product useful in the practice of the method of the present invention is prepared from a mixture of the following ingredients:

TABLE II

| Ingredient | % By Weight |
|---|---|
| Water | 25–30 |
| Lungs, Beef Lobes | 40–45 |
| Liver | 6–10 |
| Chicken | 5–8 |
| Rice | 4–8 |
| Fish Oil (omega-3 and omega-6 fatty acid source) | 5–8 |
| Cellulose | 0.5–2 |
| Beef Pulp | 0.5–2 |
| Inorganic Salts (calcium carbonate, iron oxide, potassium citrate) | 0.5–2 |
| Arginine | 0.2–0.6 |

TABLE II-continued

| Ingredient | % By Weight |
|---|---|
| Vitamins | 0.01–0.2 |
| Taurine | 0.02–0.2 |
| Minerals | 0.01–0.2 |

In preparing a pet food product useful in the practice of the present invention, the nutrient composition is adjusted so that the concentration of omega-3 polyunsaturated fatty acids is present in the animal food product of the present invention at a concentration of about 2.5 to about 7.5% on a dry matter basis and preferably about 7.0 to about 7.5% on a dry matter basis, when the omega-6 polyunsaturated fatty acids are present in the pet food product at a concentration of about 2.0 to about 6.0% on a dry matter basis.

The omega-3 and omega-6 polyunsaturated fatty acids are most conveniently provided by fish oils such as menhaden, mackerel, herring, anchovy and salmon which all have significant levels of omega-3 and omega-6 polyunsaturated fatty acids. Omega-3 polyunsaturated fatty acids C20:5 eicosapentaenoic acid and C22:6 docosahexaneoic acid are typical of fish oil and together comprise about 25–38% by weight of the fish oil. Omega-6 polyunsaturated fatty acids include linoleic acid and arachidonic acid and are present in the fish oils at lesser concentrations generally less than about 10% by weight.

The pet food product of the present invention is supplemented with arginine to contain about 2.0 to about 3.5% on a dry matter basis and preferably about 3.0 to about 3.5% on a dry matter basis. The arginine and fish oil components of the pet food product of the present invention are incorporated in the food product during the processing of the formulation, as for example, during and after mixing of the ingredients of the pet food. Distribution of these components can be accomplished by conventional means.

Other additives may be included in this pet food as needed. These other additives include flavoring, vitamins, minerals, coloring and mixtures thereof. These additives are added for nutritional purposes and palatability. Suitable amounts are easily determined by a person having ordinary skill in the art. However, up to about 5% of these ingredients are customarily used. Ingredients in this category are exemplified by iron oxide, sodium chloride, potassium citrate, potassium chloride, and other edible salts, flavoring, vitamins, minerals and coloring.

The pet food products prepared in accordance with the practice of the present invention are prepared by mixing ground animal and poultry proteinaceous tissues with the remaining ingredients which include fish oils, arginine, cereal grains and other nutritionally balancing ingredients and special purpose additives such as vitamin and mineral mixtures, inorganic salts, cellulose and beet pulp bulking agents and the like. Water sufficient for processing is also added. A vessel suitable for heating while blending the components is used.

Heating of the ingredient mix may be effected in any suitable manner as, for example, by direct steam injection or by using a vessel fitted with a heat exchanger. Following the addition of the last ingredient, the mixture is heated to a temperature ranging from approximately 70° F. to about 140° F. Temperatures outside of this range are acceptable but may not be commercially practical without the use of other processing aids. When heated to the appropriate temperature, the material is in the form of a thick liquid. The thick liquid product is then filled into cans. A lid is applied and the container is hermetically sealed. Next, the sealed can is placed into conventional equipment designed to sterilize the contents. This is usually accomplished by heating to temperatures above 230° F. for an appropriate time which is dependent on the exact temperature and formula.

For the purposes of a complete understanding of the present invention it should be recognized that the term pet food composition is generally intended to apply to commercially sold and nutritionally balanced pet food which provides the sole food intake for the pet animal.

The following Example is intended to describe specific but non-limiting embodiments of the present invention.

EXAMPLE

Preparation of Pet Food Product

A pet food product useful in the practice of the present invention was prepared by blending a mixture of the ingredients listed in Table III below and heating the mixture to 135° F. for 15 minutes followed by filling cans at 110° F. to form a thick liquid which was canned and sterilized at 250° F. for 83 minutes.

TABLE III

INGREDIENT COMPOSITION OF PET FOOD PRODUCT

| Ingredient | pounds/100 pounds |
|---|---|
| Lungs, Beef | 44.00 |
| Water | 26.12 |
| Liver, Pork | 8.00 |
| Rice, Parboiled | 6.00 |
| Menhaden Fish Oil (I) | 5.75 |
| Chicken, Mechanically Deboned | 5.50 |
| Natural Flavor* | 1.50 |
| Cellulose | 1.00 |
| Beef Pulp | 1.00 |
| Potassium Citrate | 0.50 |
| L-Arginine | 0.30 |
| Calcium Carbonate | 0.10 |
| Vitamin mix** | 0.08 |
| Mineral Mix*** | 0.05 |
| Taurine | 0.05 |
| Red Iron Oxide | 0.03 |
| Choline Chloride | 0.02 |
| TOTAL | 100.00 |

*Available from Applied Food Biotechnologies
**Available from Roche Animal Health and Nutrition
***Available from J. M. Huber Corporation

| (I) Fatty Acid Composition of Menhaden Oil**** | Wt. % of Fatty Acid |
|---|---|
| Palmitic (16:0) | 16.2 |
| Palmitoleic (16:1) | 11.6 |
| Stearic (18:0) | 2.9 |
| Oleic (18:1) | 10.9 |
| Linoleic (18:2) | 1.2 |
| Linolenic (18:3) | 1.6 |
| Octadecatetraenoic (18:4) | 3.2 |
| Eicosapentaenoic (20:5) | 14.1 |
| Docosahexaenoic (22:6) | 11.9 |
| Eicosanoic (20:1) | 1.3 |
| Arachidonic (20:4) | 1.7 |
| Docosapentaenoic (22:5) | 2.4 |

****Commercially available from Zapata Protein, Inc. Fatty acid concentrations <1% are not included Analysis of the retorted pet food product prepared from the ingredients of Table III indicated, as recorded in Table IV indicated the presence of the following constituents:

TABLE IV

NUTRIENT COMPOSITION OF PET FOOD PRODUCT

| Nutrient | % by Weight | % Dry Matter |
|---|---|---|
| Moisture | 71.6 | N/A |
| Protein | 10.7 | 37.8 |
| Fat | 9.3 | 32.6 |
| Carbohydrate | 6.1 | 21.4 |
| Fiber, crude | 1.0 | 3.5 |
| Ash | 1.3 | 4.7 |
| Calcium | 0.15 | 0.54 |
| Phosphorus | 0.14 | 0.49 |
| Sodium | 0.08 | 0.28 |
| Potassium | 0.30 | 1.1 |
| Magnesium | 0.01 | 0.04 |
| Chloride | 0.11 | 0.4 |
| Omega-6 Polyunsaturated Fatty Acid | 0.6 | 2.3 |
| Omega-3 Polyunsaturated Fatty Acid | 2.07 | 7.3 |
| Arginine | 0.89 | 3.2 |

To determine the effect of the food composition described in Table IV in reducing damage to normal skin and mucosa cells when fed to dogs with cancer undergoing radiation therapy, twelve dogs with histologically confirmed malignant neoplasia of the nasal cavity were selected sequentially from a patient population drawn from a Comparative Oncology Unit at a State University. Dogs were excluded from this study if they were cachectic or if they had received chemotherapy, exogenous steroids, or anesthesia in the 30 days before selection for the study. In addition, dogs with concurrent diseases such as renal failure, hepatic cirrhosis, endocrine diseases, obesity, or hypercalcemia were excluded.

All dogs were entered into a study of double-blind randomized design and fed one of two diets designated "Diet 1" and "Diet 2". The diets were isocaloric providing 6.1 kJ metabolizable energy/g. Each dog was exclusively fed isocaloric amounts (maintenance energy requirement (kcal =2[70 weight kg 0.75]) of one of the two diets included in the study. Diet 1 had an ingredient composition of the present invention as described in Table IV. Diet 2, the control diet, was identical to Diet 1 except soybean oil was substituted for the menhaden fish oil and arginine ingredients present in Diet 1, so Diet 2 contained lower levels of omega-3 fatty acids and arginine than Diet 1. Evaluation periods were baseline 1 week prior to the start of radiation therapy (designated "Day 0"), 7 days into radiation therapy, and 21 and 42 days after radiation therapy was completed.

The serum fatty acid concentrations of the omega-3 and omega-6 fatty acids in blood drawn from the patients over the evaluation period are recorded in Table V below.

TABLE V

Serum Fatty Acid Concentrations

| | Elapsed time in days | | | |
|---|---|---|---|---|
| | 0 | 7 | 21 | 42 |
| | Serum Concentration ($\mu$mol/L) | | | |
| Omega 3 Fatty Acids | | | | |
| Docosahexaenoic Acid (C22:6) | | | | |
| Diet 1 | 1.95 | 21.13 | 18.70 | 22.81 |
| Diet 2 | 3.96 | 5.16 | 3.48 | 3.66 |
| Eicosapentaenoic Acid (C20:5) | | | | |
| Diet 1 | 1.03 | 17.95 | 18.0 | 25.93 |
| Diet 2 | 1.16 | 0.80 | 1.02 | 1.10 |

TABLE V-continued

Serum Fatty Acid Concentrations

| | Elapsed time in days | | | |
|---|---|---|---|---|
| | 0 | 7 | 21 | 42 |
| | Serum Concentration ($\mu$mol/L) | | | |
| Omega-6 Fatty Acids | | | | |
| Linoleic Acid (C18:2) | | | | |
| Diet 1 | 73.92 | 34.45 | 31.26 | 25.96 |
| Diet 2 | 62.84 | 88.32 | 69.12 | 58.26 |

The data recorded in Table V show that dogs fed Diet 1, the diet of the present invention, had significantly (p<0.001) higher serum levels of the omega-3 polyunsaturated fatty acids, docosahexaenoic acid (C22:6) and eicosapentaenoic acid (C20:5); and reduced concentrations of the omega 6 polyunsaturated fatty acid, linoleic acid (C18:2) as compared to baseline (Day 0) and dogs fed Diet 2.

These increased serum omega-3 polyunsaturated fatty acids, docosahexaneoic (C22:5) and eicosapentaenoic (C20:5) levels were determined to be significantly (p =statistical significance of difference from zero) associated with lower tissue concentrations of inflammatory mediators as reported in Tables VI and VII which follow. The level of inflammatory mediators provide biochemical evidence of decreased damage to skin and mucosa.

Study parameters examined to evaluate the effect of Diet 1 and Diet 2 on ameliorating radiation damage were the generation of inflammatory mediators prostaglandin $E_2$, ($PGE_2$), 11-dehydrothromboxane $B_2$ (11 DTX $B_2$), as well as histologic scores evaluated from 6 mm punch biopsies taken from the skin and oral mucosa from areas of high (300 cGy) and low (200 cGy) daily radiation dosages are recorded in Tables VI–VII below.

Table VI below records the presence in a sample taken from the inner lip (oral mucosa) of the patient of the inflammatory mediators $PGE_2$ and $11DTXB_2$ which are biochemical markers for inflammation.

TABLE VI

Rank correlation of serum fatty acids with oral mucosal inflammatory mediators

| | | Oral Mucosal Inflammatory Mediators | |
|---|---|---|---|
| | | $PGE_2$ | $11DTXB_2$ |
| Omega-3 Fatty Acids | | | |
| Docosahaexaenoic Acid (C22:6) | Coefficient of correlation p | -0.11299 0.2313 | -0.15750 0.0942 |
| Eicosapentaenoic Acid (C20:5) | Coefficient of correlation p | -0.22354 0.0168 | -0.21390 0.0223 |
| Omega-6 Fatty Acids | | | |
| Linoleic Acid (C18:2) | Coefficient of correlation p | 0.04855 0.6079 | 0.31450 0.0007 |

The data recorded in Table VI show a negative correlation for the omega-3 polyunsaturated fatty acids, docosahexaenoic and eicosapentaenoic acids, that is, the higher the omega-3 fatty acid level present in the sample the lower the inflammation encountered by the patient. The data further show a positive correlation for the omega-6 fatty acid, linoleic acid, namely, the higher the omega-6 polyunsaturated fatty acid level, the higher the mediator level and the higher the level of inflammation encountered by the patient.

Table VII below records the presence, in a sample taken from the skin surface of the patient, of the inflammatory mediators $PGE_2$ and 11DTX $B_2$.

TABLE VII

Rank correlation of serum fatty acids with skin inflammatory mediators

|  |  | Skin Inflammatory Mediators | |
| --- | --- | --- | --- |
|  |  | $PGE_2$ | $11DTXB_2$ |
| Omega-3 Fatty Acids |  |  |  |
| Docosahexaenoic Acid (C22:6) | Coefficient of correlation<br>p | −0.13259<br>0.0596 | −0.16783<br>0.0769 |
| Eicosapentaenoic Acid (C20:5) | Coefficient of correlation<br>p | −0.2729<br>0.0040 | −0.16456<br>0.0829 |
| Omega-6 Fatty Acids |  |  |  |
| Linoleic Acid (C18:2) | Coefficient of correlation<br>p | 0.15504<br>0.0995 | 0.23658<br>0.0120 |

The data recorded in Table VII shows that skin concentrations of inflammatory mediators were statistically significantly lower by rank correlation in patients with high levels of the omega-3 fatty acids, eicosapentaenoic and docosahexaenoic acids. Lower concentrations of inflammatory mediators are believed to play a role in ameliorating acute side effects of radiation therapy.

The data recorded in Table VIII below indicate that serum docosahexaenoic and eicosapentaenoic acid levels are also significantly associated with histologic evidence of decreased damage to the oral mucosa. Eicosapentaenoic and docosahexaenoic acid serum concentrations were determined to be positively correlated with cell thickness in mucosal areas, eicosapentaenoic acid (p=0.0171) and docosahexaenoic acid (p=0.0241).

TABLE VIII

Rank correlation of serum fatty acids with histology score of oral mucosal cells

|  |  | Histology Score for Oral Mucosa Cells |
| --- | --- | --- |
| Omega-3 Fatty Acids |  |  |
| Docosahexaenoic Acid (C22:6) | Coefficient of correlation<br>p | 0.25664<br>0.0171 |
| Eicosapentaenoic Acid (C20:5) | Coefficient of correlation<br>p | 0.24314<br>0.0241 |
| Omega-6 Fatty Acids |  |  |
| Linoleic Acid (C18:2) | Coefficient of correlation<br>p | −0.3776<br>0.2059 |

The data recorded in Table VIII shows that the patients with the overall highest eicosapentaenoic and docosahexaenoic acid serum concentrations had the best histological cell layer thickness scores in mucosal areas which is believed to provide for decreasing mucositis, thus improving quality of life in patients undergoing radiation therapy.

Quality of life in these cancer patients undergoing radiation therapy was further assessed using a clinical performance-scoring scheme where a lower score indicates better clinical performance. As shown in Table IX, serum eicosapentaenoic and docosahexaenoic acid had a significant negative rank correlation with clinical performance status, that is, the higher the omega-3 fatty acid level present in the sample the lower the score on clinical performance scoring scheme indicating better clinical performance.

TABLE IX

Rank correlation of serum fatty acids with clinical performance status

|  |  | Clinical Performance |
| --- | --- | --- |
| Omega-3 Fatty Acids |  |  |
| Docosahexaenoic Acid (C22:6) | Coefficient of correlation<br>p | −0.36840<br>0.0139 |
| Eicosapentaenoic Acid (C20:5) | Coefficient of correlation<br>p | −0.31893<br>0.0349 |
| Omega-6 Fatty Acids |  |  |
| Linoleic Acid (C18:2) | Coefficient of correlation<br>p | 0.22244<br>0.1467 |

The procedures for analysis from which the data recorded in Tables V–VIII were obtained are described below.

Fatty Acid Analysis

Fatty Acids were analyzed following the procedure of Zicker et al as described in Ohta A, Mayo M C, Kramer N, Lands WE. *Rapid analysis of fatty acids in plasma lipids.* Lipids 1990; 25: 742–747.

Histopathology

The oral mucosa and skin were biopsied with a 6 mm Baker's biopsy punch in areas receiving low (200 cGy) and high (300 cGy) radiation dosages as determined by computerized treatment planning. Biopsies were performed 1 week prior to therapy, 1 day into therapy, 7 days into therapy, at the end of therapy, and 21 days after therapy was completed. Tissues were evaluated histopathologically by a single pathologist for cell layer thickness.

Inflammatory Mediator Analysis

Oral mucosa and skin from areas receiving low and high radiation dosage were obtained the same as for histopathology and frozen at −80° C. Frozen samples were placed on a clean glass slide and cut into small pieces before thawing could occur. Cut pieces were transferred into a 4 ml plastic culture tube and 2 ml of cold ethyl acetate was added. The sample was then homogenized at highest speed setting for one minute while sample and culture tube were sitting in an ice bath. Sample and culture tubes were then removed from the homogenizer and the homogenizer tip was rinsed with one ml cold ethyl acetate. Rinse and sample were combined. Culture tubes were capped with aluminum foil and set in an ice bath for 30 minutes. After thirty minutes in ice bath, the tubes were capped and centrifuged at 500 g for ten minutes at five degrees C. All supernatant was removed and put into a new four ml plastic culture tube. Ethyl acetate was evaporated from the sample with a slow stream of nitrogen gas. A warm (30° C.) water bath was used to facilitate drying. Sample residue was resuspended in 500 ul EIA buffer (Caymen, Ann Arbor, Mich.). The sample was capped with nitrogen gas and stored at −80° C. Samples were analyzed for prostaglandin $E_2$ and, 11-dehydro-Thromboxane B2 with Enzyme Immunoassay kits (Caymen, Ann Arbor, Mich.).

What is claimed is:

1. A method for mitigating the damaging effects to normal skin and mucosa cells of a pet animal undergoing radiation therapy of malignant neoplasia comprising preparing a nutritionally balanced pet food composition comprising omega-6 polyunsaturated fatty acids, supplementing the food composition with a mixture of omega-3 polyunsaturated fatty acids and arginine exposing the animal to radiation therapy and feeding the food composition to the animal at least during the period of time during which the animal is exposed to the radiation whereby radiation damage to the animals normal cells is mitigated.

2. The method of claim 1 wherein the omega-3 polyunsaturated fatty acids are present in the food composition at a concentration of about 2.5 to abut 7.5% on a dry matter basis.

3. The method of claim 1 wherein arginine is present in the food composition at a concentration of about 2.0 to about 3.5% on a dry matter basis.

4. The method of claim 1 wherein the weight ratio of omega-3 polyunsaturated fatty acids to omega-6 fatty acids present in the food is about 0.3:1 to 3.5:1.

5. The method of claim 1 wherein the nutritionally balanced food has a fat content of about 27 to 35% on a dry matter basis, a carbohydrate content of about 15 to abut 27% on a dry matter basis and the weight ratio of omega-3 to omega-6 polyunsaturated fatty acids being in the range of about 0.3:1 to 3.5:1.

* * * * *